(12) United States Patent
Hirano et al.

(10) Patent No.: US 9,123,163 B2
(45) Date of Patent: Sep. 1, 2015

(54) MEDICAL IMAGE DISPLAY APPARATUS, METHOD AND PROGRAM

(75) Inventors: Masaharu Hirano, Setagaya-ku (JP); Futoshi Sakuragi, Minato-ku (JP); Jun Masumoto, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 422 days.

(21) Appl. No.: 13/498,857

(22) PCT Filed: Sep. 29, 2010

(86) PCT No.: PCT/JP2010/005865
§ 371 (c)(1),
(2), (4) Date: Mar. 28, 2012

(87) PCT Pub. No.: WO2011/040015
PCT Pub. Date: Apr. 7, 2011

(65) Prior Publication Data
US 2012/0188240 A1    Jul. 26, 2012

(30) Foreign Application Priority Data

Sep. 30, 2009  (JP) ................................. 2009-226501

(51) Int. Cl.
G06T 15/00   (2011.01)
G06T 15/08   (2011.01)
G06T 19/00   (2011.01)
A61B 6/00    (2006.01)

(52) U.S. Cl.
CPC .................. G06T 15/08 (2013.01); G06T 19/00 (2013.01); *A61B 6/463* (2013.01); *A61B 6/504* (2013.01); *G06T 2215/06* (2013.01)

(58) Field of Classification Search
CPC ...................... G06T 15/08; G06T 2207/10072; G06T 7/0012; G06T 2219/028; G06T 11/008; G06T 2207/3004; G06T 2207/30101; G06T 2207/30028; G06T 2207/30061; G06T 2207/30096; G06T 15/00; G06T 2207/10132; G06T 2207/30004; G06T 2210/41; G06T 2207/20216; G06T 17/00; G06T 19/00; G06T 2207/30016; G06T 2207/30021; G06T 2207/30048; G06T 2207/30052; G06T 2207/30056; G06T 2207/30088; G06T 2215/06; A61B 6/463; A61B 6/504
USPC ........... 345/419, 501, 619; 382/128, 130, 131
See application file for complete search history.

(56) References Cited

U.S. PATENT DOCUMENTS

| | | | |
|---|---|---|---|
| 2004/0013290 A1 | 1/2004 | Krishnan et al. | |
| 2004/0249270 A1* | 12/2004 | Kondo et al. | 600/425 |
| 2009/0129635 A1* | 5/2009 | Abe | 382/115 |

FOREIGN PATENT DOCUMENTS

| | | | |
|---|---|---|---|
| JP | 2004-283373 A | 10/2004 | |
| JP | 2005-518915 A | 6/2005 | |
| JP | 2006-075390 A | 3/2006 | |
| JP | 2006-198060 A | 8/2006 | |
| JP | 2007-135843 A | 6/2007 | |
| JP | 2007-151881 A | 6/2007 | |

* cited by examiner

*Primary Examiner* — Ke Xiao
*Assistant Examiner* — Kim-Thanh T Tran
(74) *Attorney, Agent, or Firm* — Sughrue Mion, PLLC

(57) ABSTRACT

A medical image display apparatus includes an image obtainment unit configured to obtain a first image and a second image of a subject generated based on volume data, a base line setting unit configured to set a base line in the first image obtained by the image obtainment unit, an image division unit configured to divide, based on the base line that has been set in the first image by the base line setting unit, the second image into two divided images, and a display control unit configured to display the two divided images, which have been divided by the image division unit, on the first image at a display device in such a manner that the two divided images are away from the base line by a predetermined distance.

10 Claims, 4 Drawing Sheets

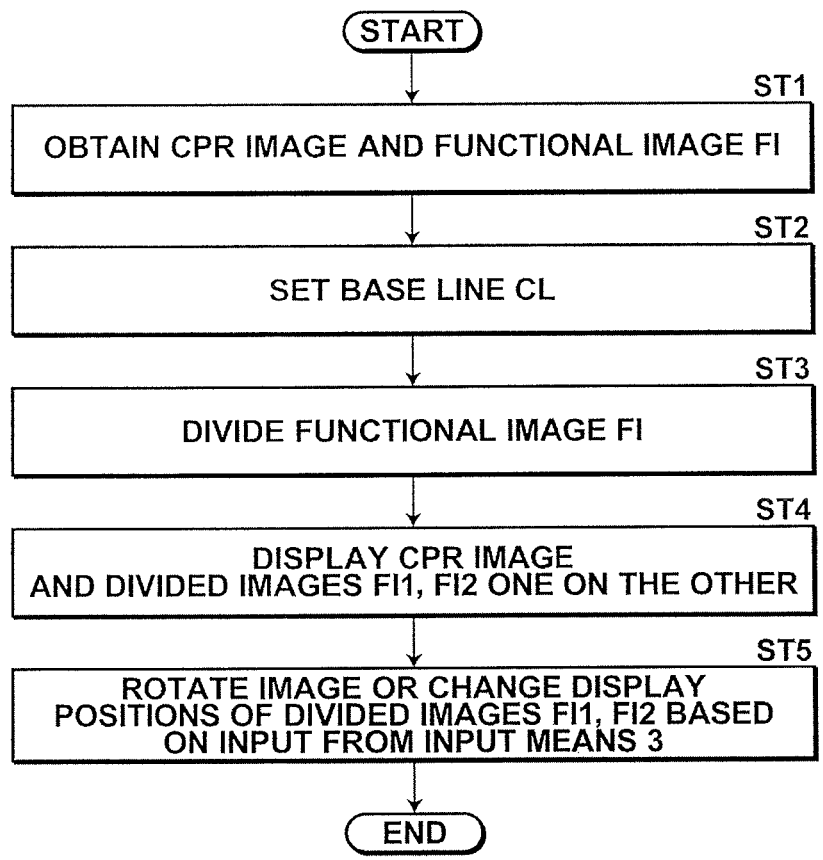

MEDICAL IMAGE DISPLAY APPARATUS, METHOD AND PROGRAM

CROSS REFERENCE TO RELATED APPLICATIONS

This application is a National Stage of International Application No. PCT/JP2010/005865 filed Sep. 29, 2010, claiming priority based Japanese Patent Application Nos. 2009-226501, filed Sep 30, 2009 the contents of all of which are incorporated herein by reference in their entirety.

BACKGROUND OF THE INVENTION

1. Field of the Invention

The present invention relates to a medical image display apparatus, method and program for displaying three-dimensional volume data and a functional image of a subject.

2. Description of the Related Art

Conventionally, a medical image display apparatus having a mode for observing the inner wall of a lumen of a subject as if seeing it from the inside of the lumen has been known. In this mode, an image of a three-dimensional structure is obtained by volume rendering based on three-dimensional digital data of an object obtained by CT or the like, and an image resembling an endoscopic image is generated based on the three-dimensional volume data to observe a lesion in a tubular organ, such as a blood vessel, intestines, bronchi and an artery, of the subject. Further, as three-dimensional image processing, MIP (Maximum Intensity Projection) processing, MinIP (Minimum Intensity Projection) processing, MPR (Multi Planar Reconstruction) processing, CPR (Curved Planaer Reconstruction) processing, and the like are known. Especially, the CPR processing selects an arbitrary surface in three-dimensional volume data, and reconstructs a two-dimensional image from a three-dimensional image along the selected surface. Accordingly, with respect to the morphology of the inner wall of a tubular structure, such as a large intestine and a blood vessel for example, it is possible to display a cross section of the tubular structure in a longitudinal direction thereof on a display screen (for example, please refer to Japanese Unexamined Patent Publication No. 2007-135843 (Patent Document 1) and Japanese Unexamined Patent publication No. 2004-283373 (Patent Document 2)).

Besides a morphological image obtained from the CT apparatus or the like, and which represents the morphology of the subject, a functional image representing the function of the subject is provided for a user. As the functional image, for example, a SPECT image obtained by Single Photon Emission Tomography, a PET image obtained by Positron Emission Tomography, an analysis result, such as a bull's eye image, obtained by analyzing a morphological image and a functional image, and the like are known.

As a method for displaying the aforementioned morphological image and functional image, a method for displaying the morphological image and the functional image one on the other is known (for example, please refer to Japanese Unexamined Patent Publication No. 2006-198060 (Patent Document 3)). Patent Document 1 discloses displaying a functional image and a morphological image one on the other after a relative positional relationship between the functional image and the morphological image is obtained, and coordinate transformation is performed to match the size of the functional image and that of the morphological image based on the relative positional relationship.

However, when the functional image and the morphological image are simply placed one on the other as disclosed in Patent Document 1, the function of each region of a subject may be recognized, but there is a problem that the efficacy of diagnosis becomes lower because the morphology of the subject is hard to recognize. For example, when a SPECT image or the like is displayed on a CPR image of a blood vessel or the like obtained from a morphological image, such as a CT image, if the SPECT image or the like is simply displayed in such a manner to be placed directly on the CPR image, observation of morphology information, such as a stenosis condition and a plaque site of a blood vessel, becomes difficult because the images are placed one on the other. Meanwhile, even if the functional image and the morphological image are separately displayed, there is a problem that the function of each region is not recognizable at a glance.

SUMMARY OF THE INVENTION

In view of the foregoing circumstances, it is an object of the present invention to provide a medical image display apparatus, method and program that can make it possible to efficiently recognize both of morphology information and function information about a subject.

A medical image display apparatus of the present invention is characterized by comprising:

an image obtainment means that obtains a first image and a second image of a subject generated based on volume data;

a base line setting means that sets a base line in the first image obtained by the image obtainment means;

an image division means that divides, based on the base line that has been set in the first image by the base line setting means, the second image into two divided images; and a display control means that displays the two divided images, which have been divided by the image division means, on the first image at a display device in such a manner that the two divided images are away from the base line by a predetermined distance.

A medical image display method of the present invention is characterized by comprising the steps of:

obtaining a first image and a second image of a subject generated based on volume data;

setting a base line in the obtained first image;

dividing, based on the base line that has been set in the first image, the second image into two divided images; and displaying the two divided images, which have been divided, on the first image at a display device in such a manner that the two divided images are away from the base line by a predetermined distance.

A medical image display program of the present invention is a program for causing a computer to execute the procedures of:

obtaining a first image and a second image of a subject generated based on volume data;

setting a base line in the obtained first image;

dividing, based on the base line that has been set in the first image, the second image into two divided images; and displaying the two divided images, which have been divided, on the first image at a display device in such a manner that the two divided images are away from the base line by a predetermined distance.

Here, the term "subject" means, for example, each tissue of a human body, such as epithelial tissue, connective tissue, muscle tissue, and nervous tissue, and a tubular object, such as a blood vessel, intestines, bronchi, an artery, and a coronary artery.

Further, the first image and the second image may be any images as long as they are generated based on sets of volume data different from each other or based on the same volume data. For example, the first image may be a morphological image representing morphology information about a subject, and the second image may be a functional image representing function information about the subject. The functional image is, for example, a SPECT image obtained by Single Photon Emission Tomography, a PET image obtained by Positron Emission Tomography, an analysis result obtained by analyzing a morphological image and a functional image, and the like.

Specifically, the morphological image should be an image representing morphology information about a subject. The morphological image may be a CPR image of a tubular object, as a subject. At this time, a base line setting means sets a core line of the tubular object as a base line. The term "core line" means a center line of the tubular object connecting a center (center of gravity) of each cross section of the tubular object. A known technique may be used to extract the core line.

Further, the functional image may represent the function of a surface that is orthogonal to a core line, and which is independent from the surface of the CPR image. At this time, the display control means may include, a rotation display means that rotates the CPR image with respect to the core line, as a rotation axis, and displays the rotated image. Even when the CPR image has been rotated and displayed by the display control means, the display of the functional image may be unchanged.

Further, the display control means may have a function for adjusting a distance from the first divided functional image to the core line and a distance from the second divided functional image to the core line based on an input at an input means.

According to the medical image display apparatus, method and program of the present invention, a first image and a second image of a subject generated based on volume data are obtained, and the obtained first image and second images are placed one on the other. Further, a base line is set in the first image, and the second image that is placed on the first image is divided, based on the set base line, into two divided images. The two divided images, which have been divided, are displayed on the first image at positions away from the base line by a predetermined distance. Accordingly, it is possible to set the base line in an area that a user wants to observe in the first image, and to avoid placing the second image on an area in the vicinity of the base line in the first image. Therefore, it is possible to prevent observation of an area in which a user wants to observe the morphology from becoming difficult because of the functional image. Further, it is possible to improve the efficiency of diagnosis because both of the first image and the second image become observable at a glance.

Further, when the display control means has a function for adjusting a distance between two divided images based on an input at the input means, it is possible to arrange the images in such a manner that a user can most easily observe morphology information and a functional image corresponding to the morphology information.

Further, when the functional image represents, along a core line, the function of a surface that is orthogonal to the core line, and which is independent from a surface of a CPR image, and the display control means has a rotation display means that rotates the CPR image that is the first image with respect to the core line, as a rotation axis, and displays the rotated CPR image, and a display of the functional image is not changed even when the rotation display means has rotated the CPR image and displayed the rotated CPR image, it is possible to recognize the condition of the subject based on a functional image, such as an influence of a stenosis of a coronary artery, at a glance while rotating only the morphological image.

BRIEF DESCRIPTION OF THE DRAWINGS

FIG. 7 is a flowchart illustrating a desirable embodiment of an endoscopic image processing method of the present invention.

DESCRIPTION OF THE PREFERRED EMBODIMENTS

Figure 1:
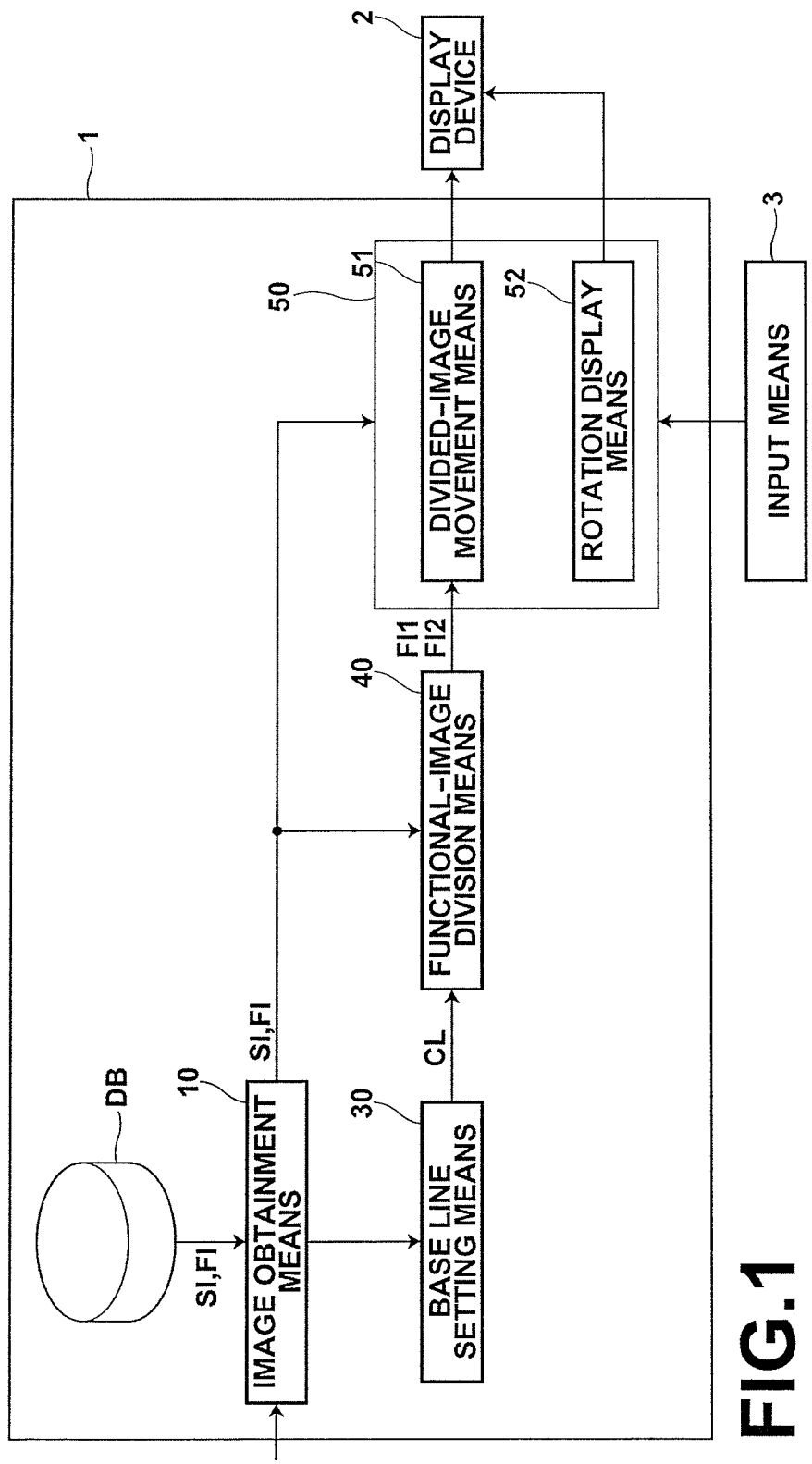
FIG. 1 is a block diagram illustrating a desirable embodiment of a medical image display apparatus of the present invention.

Hereinafter, embodiments of a medical image display apparatus of the present invention will be described in detail with reference to drawings. FIG. 1 is a schematic diagram illustrating the configuration of a medical image display apparatus 1 of the present invention. The configuration of the medical image display apparatus 1, as illustrated in FIG. 1, is realized by causing a computer to execute a medical image display program that has been read in an auxiliary storage device. At this time, the medical image display program is recorded in a recording medium, such as a CD-ROM, or distributed through a network, such as the Internet, and installed in the computer.

Figure 2:
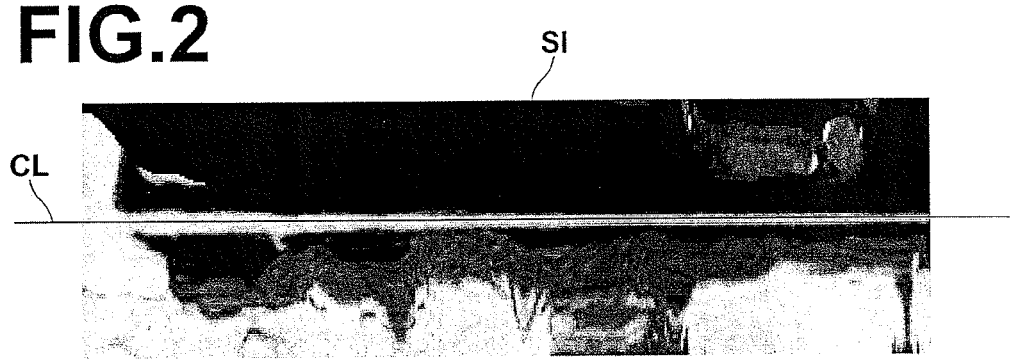
FIG. 2 is a diagram illustrating an example of a morphological image obtained by an image obtainment means illustrated in FIG. 1.

The medical image display apparatus 1 illustrated in FIG. 1 includes an image obtainment means 10, a base line setting means 30, an image division means 40, and a display control means 50. The image obtainment means 10 obtains first image SI and second image FI of subject S that have been generated based on volume data. Hereinafter, in the embodiments of the present invention, a case in which the first image SI is a morphological image representing morphology information about the subject, and the second image FI is a functional image FI representing function information about the subject S will be described as an example. Here, the morphological image SI is a CPR image, as illustrated in FIG. 2. The CPR image is generated by obtaining volume data about a tubular object, such as a blood vessel, based on an image obtained by a CT apparatus or the like, and by performing CPR (Curved Planaer Reconstruction) processing on the volume data. A known technique may be used to generate the CPR image. For example, please refer to Japanese Unexamined Patent Publication No. 2004-283373. FIG. 2 illustrates a case of displaying an image in so-called straight view mode. Alternatively, the image may be displayed in stretch view mode.

The image obtainment means 10 may obtain a CPR image stored in image database DB. Alternatively, the image obtainment means 10 may obtain a CPR image generated by a CPR image obtainment means, which is not illustrated. The CPR image obtainment means generates the CPR image based on volume data stored in image database DB by using a known technique.

When the morphological image SI and the functional image FI are generated based on sets of volume data different from each other (for example, volume data based on a CT image and volume data based on a PET image), the image obtainment means 10 obtains the morphological image SI and the functional image FI after performing registration (coordinate transformation) between the different sets of volume data. Alternatively, the image obtainment means 10 obtains the morphological image SI and the functional image FI that have been generated based on respective sets of volume data in image database DB on which registration has been performed. A case in which the morphological image SI and the functional image FI are generated after registration between the different sets of volume data is performed will be described as an example. Alternatively, registration between the morphological image SI and the functional image FI may be performed after the morphological image SI and the functional image FI are obtained. Further, the image obtainment means 10 may perform registration between the morphological image SI and the functional image FI with respect to the direction of core line CL.

Meanwhile, the functional image FI means an image representing a result of function analysis on the morphological image SI, an image, such as a SPECT image obtained by Single Photon Emission Tomography and a PET image obtained by Positron Emission Tomography, representing the function of subject S by using a different imaging technique from the morphological image FI, and an image representing a result of analyzing the PET image and the like.

Figure 3:
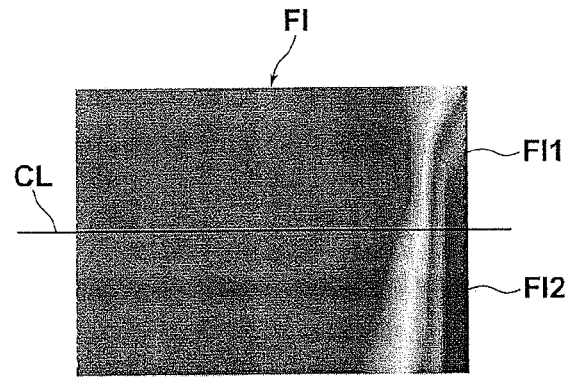
FIG. 3 is a diagram illustrating an example of a functional image obtained by the image obtainment means illustrated in FIG. 1.
Figure 4:
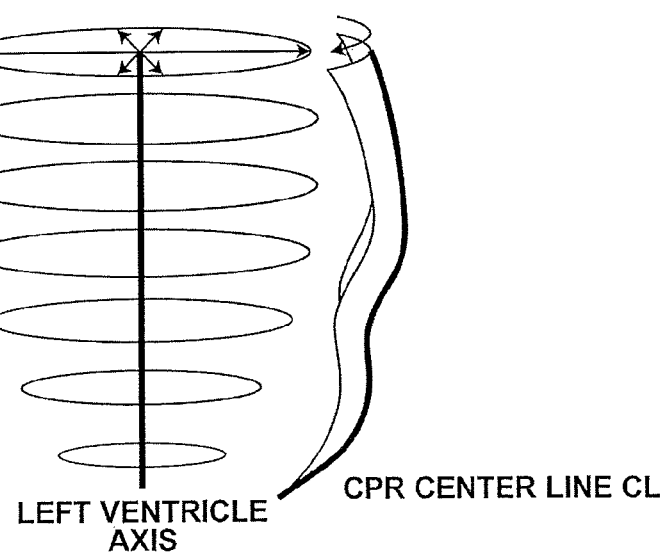
FIG. 4 is a schematic diagram illustrating an example of a function of a surface represented by the functional image illustrated in FIG. 3.

The functional image FI is, for example, an image representing a function of a slice surface orthogonal to core line CL of subject S, as illustrated in FIG. 3, or an image obtained by developing, along the core line CL, the function of each region of the subject S onto a plane. Specifically, the functional image FI illustrated in FIG. 3 represents, for example, a result of function analysis on a surface in the vicinity of core line CL in a CPR image of a coronary artery, and the surface being formed based on the axis of a left ventricle, as illustrated in FIG. 4.

The image obtainment means 10 may obtain the functional image FI stored in the image database DB. Alternatively, the image obtainment means 10 may obtain functional image FI that has been analyzed by a function analysis means, which is not illustrated. The function analysis means uses volume data and a functional image, such as a PET image, and performs analysis by using a known technique.

Figure 5:
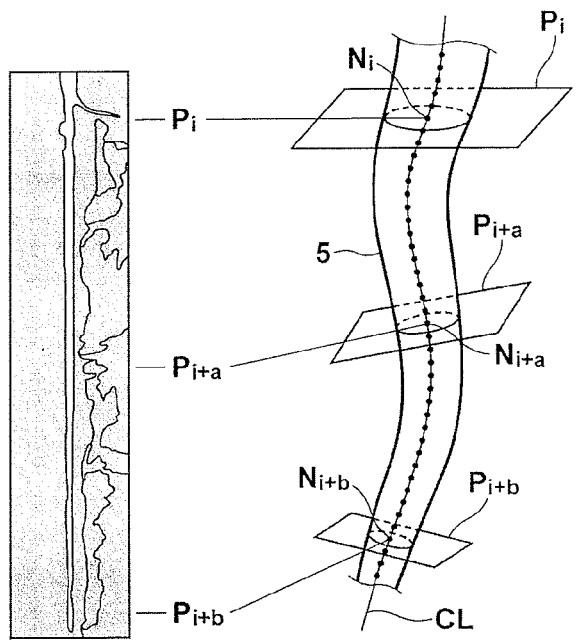
FIG. 5 is a schematic diagram illustrating a manner of generating a CPR image illustrated in FIG. 2.

Here, generation of a CPR image (please refer to FIG. 2) will be described by using a coronary artery, as an example. First, the positions of plural candidate points Ni constituting the core line of the coronary artery and a principal axis direction are calculated based on the values of voxel data constituting the volume data. Alternatively, the positions of plural candidate points Ni constituting core line CL of the coronary artery and a principal axis direction are calculated by calculating Hessian matrix with respect to volume data, and by analyzing the eigenvalue of the calculated Hessian matrix. Further, a feature value representing the likelihood of a coronary artery is calculated with respect to voxel data in the vicinity of candidate point Ni, and judgment is made as to whether the voxel data represent a coronary artery region 5 based on the calculated feature value. The judgment based on the feature value is made based on an evaluation function that has been obtained in advance, for example, by machine learning. Accordingly, the coronary artery region 5, as illustrated in FIG. 5, is extracted from the volume data.

In the process of extracting the coronary artery region 5, core line CL of the coronary artery is set, and the position of each candidate point constituting the core line CL and the principal axis direction are calculated. Therefore, it is possible to set cross section Pi (orthogonal cross section) perpendicular to the principal axis direction based on information calculated at each of the candidate points. After then, a straight CPR image is generated through a known procedure by using the coronary artery region 5, the position of each of the candidate points and the principal axis direction, the course of the core line, the position and direction of cross section P, and the like. In the present embodiment, when a blood vessel branch in which a start point and an end point of an observation range has been set is selected, a straight CPR image representing the entire range of the blood vessel branch is displayed.

The base line setting means 30 illustrated in FIG. 1 sets base line CL in the morphological image SI, and the base line CL is used when functional image FI is divided, as will be described later. As described above, when the morphological image SI is a CPR image of a tubular object, as a subject, the base line setting means 30 sets, as the base line CL, a core line of the tubular object. The base line setting means 30 may have a function for setting the base line CL in the vicinity of a region that a user wants to observe based on an input by the user at the input means 3.

The image division means 40 divides, based on core line CL, functional image FI into two images of first divided functional image FI1 and second divided functional image FI2. The display control means 50 changes the manner of displaying the morphological image SI and the functional image FI based on an input at the input means 3, such as a mouse and a keyboard. The display control means 50 includes a divided-image movement means 51 and a rotation display means 52.

The display control means 50, illustrated in FIG. 1, displays the CPR image and each of the divided functional images FI1, FI2 one on the other at the display device 2. The display control means 50 includes the divided-image movement means 51 and the rotation display means 52. As illustrated in FIG. 5, the divided-image movement means 51 adjusts the display positions of the first divided functional image FI1 and the second divided functional image FI2, which have been divided by the image division means 40, based on the core line CL. Specifically, the divided-image movement means 51 adjusts distance ΔL from the core line CL to each of the divided functional images FI1, FI2 based on an input at the input means 3. Further, it is possible to display the functional image FI and the CPR image with ΔL=0 by an input at the input means 3. Specifically, it is possible to display the functional image FI and the CPR image simply one on the other. Further, the display control means 50 displays each of the divided functional images FI1, FI2 in such a manner that an area that is placed on the morphological image SI is displayed, but an area (upper and lower outside areas in FIG. 5) that is not placed on the morphological image SI is not displayed.

When functional image FI, such as a SPECT image, is displayed on morphological image SI as described above, findings that morphology information that a user wants to observe in a CPR image is present in the vicinity of core line CL in the CPR image in many cases is considered, and the functional image FI is displayed in an area other than the vicinity of the core line CL. Accordingly, it is possible to prevent observation of morphology information, such as a stenosis condition and a plaque site of a blood vessel, from becoming difficult.

The rotation display means 52 illustrated in FIG. 1 has a function for rotating a CPR image with respect to core line CL, as a rotation axis, and displaying the rotated CPR image. At this time, the display control means 50 may maintain the display of the functional image FI without change even if the CPR image is rotated and displayed by the rotation display means 52. Accordingly, when the functional image FI represents function information at each slice plane (for example, please refer to FIGS. 3 and 4) instead of function information at each position of morphological image SI, it is possible to prevent the efficiency of diagnosis from dropping because of changing the functional image FI.

Specifically, when an analysis result obtained based on functional image FI, such as a SPECT image, is mapped on morphological image SI of a coronary artery obtained from a CT image or the like, if the analysis result with respect to an image position of the morphological image SI is simply mapped, the analysis result to be mapped changes each time when the morphological image SI is rotated. Therefore, it is difficult to observe, for example, an influence of a stenosis of the coronary artery or the like at a glance, and there is a risk of erroneously recognizing the condition, depending on rotation. For example, when the analysis result of the functional image FI is a result of analyzing a left ventricle in a direction orthogonal to the axis of the left ventricle with the axis of the left ventricle as a center (please refer to FIG. 4), the rotation display means 52 maps, on the morphological image SI, an analysis result with respect to an image position on a surface formed by rotating the course of the morphological image SI of the coronary artery with respect to the axis of the left ventricle, as a center.

Figure 6:
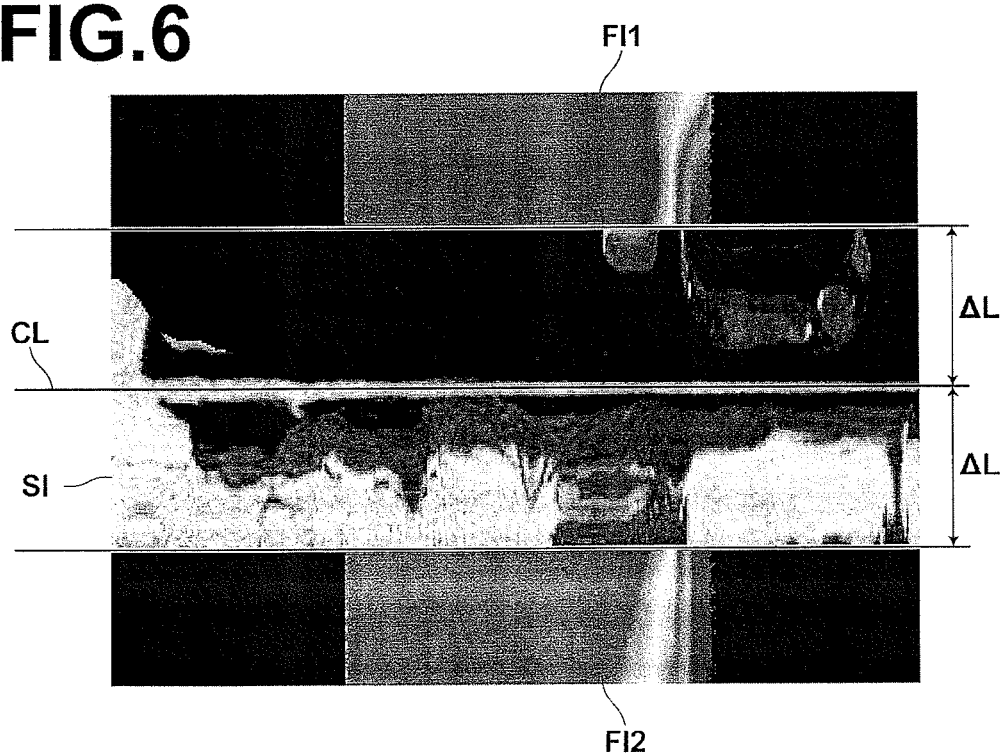
FIG. 6 is a diagram illustrating a manner of dividing a functional image based on a core line and displaying the divided images by a display control means illustrated in FIG. 1.

FIG. 6 is a flowchart illustrating a desirable embodiment of a medical image display method of the present invention. With reference to FIGS. 1 through 6, the medical image display method will be described. First, the image obtainment means 10 obtains morphological image SI and functional image FI (step ST1, please refer to FIGS. 2 and 3). After then, the base line setting means 30 sets base line CL (step ST2), and the image division means 40 divides the functional image FI into two images of first divided functional image FI1 and second divided functional image FI2 (step ST3). Then, each of the first divided functional image FI1 and the second divided functional image FI2 is displayed on the morphological image in such a manner to be away from base line CL by distance ΔL at the display device 2 (step ST4, please refer to FIG. 5).

Further, the display control means 50 displays the functional image FI based on an input at the input means 3 in such a manner that the functional image FI is divided based on core line CL (step ST5), or the display control means 50 rotates a cross-sectional position displayed by the morphological image SI without changing the display of the functional image FI.

According to each of the embodiments, first image SI and second image FI of a subject generated based on volume data are obtained, and the obtained first image SI and second image FI are placed one on the other. Further, base line CL is set in the first image SI, and the second image FI placed on the first image is divided into two divided images based on the set base line CL. The two divided images, which have been divided, are displayed on the first image SI in such a manner that each of the divided images is away from base line CL by a predetermined distance ΔL. Therefore, it is possible to display the functional image FI in such a manner that the functional image FI is not placed on the first image SI in an area in the vicinity of the base line CL by setting the base line CL in an area in which a user wants to observe morphology. Hence, it is possible to prevent observation of an area in which the user wants to observe morphology from becoming difficult because of the functional image FI. Further, it is possible to improve the efficiency of diagnosis by making recognition of morphology information and function information at a glance possible.

Further, as illustrated in FIG. 5, when the display control means 50 has a function for adjusting a distance from the first divided functional image FI1 to the core line CL and a distance from the second divided functional image FI2 to the core line CL based on an input by an input means, observation of morphological image SI and functional image FI corresponding to the morphological image SI is possible while the images are arranged in such a manner that a user can most easily observe the images.

Further, for example, as illustrated in FIG. 4, when the functional image FI represents, along a core line, a function of a surface that is independent from a surface of a CPR image orthogonal to the core line, and the display control means 50 includes the rotation display means 52 that rotates the CPR image that is the first image with respect to the core line CL, as a rotation axis, and displays the rotated image, and the display of the functional image FI is not changed even if the rotation display means 52 has rotated the CPR image and displayed the rotated CPR image, it is possible to recognize the condition of the subject based on the functional image, such as the influence of the stenosis of the coronary artery for example, at a glance while rotating only the morphological image.

The embodiments of the present invention are not limited to the aforementioned embodiments. For example, in the above embodiments, a case in which the subject is a blood vessel was described as an example. Alternatively, the subject may be a large intestine, and the like. Further, a case in which the base line setting means 30 automatically sets the core line CL as the base line was described as an example. Alternatively, a user may set the base line at a position that he/she wants to observe morphology.

Further, in the aforementioned embodiments, a case in which the first image is the morphological image SI, and the second image is the functional image FI was described as an example. Alternatively, the second image may be an image obtained in the past or an analysis result, such as a local ejection fraction, instead of the functional image FI, and such a second image and the first may be displayed one on the other. Even in this case, it is possible to recognize the first image and the second image at a glance while easily observing an area that a user wants to observe in the first image. Therefore, it is possible to improve the efficiency of diagnosis.

The invention claimed is:

1. A medical image display apparatus comprising:
   an image obtainment unit configured to obtain a first image and a second image of a subject generated based on volume data;
   a base line setting unit configured to set a base line in the first image obtained by the image obtainment unit;
   an image division unit configured to divide, based on a division line, which is set within the second image, corresponding to the base line that has been set in the first image by the base line setting unit, the second image into two divided images; and
   a display control unit configured to display the two divided images, which have been divided by the image division unit, on the first image at a display device in such a manner that the two divided images are away from the base line within the first image by a predetermined distance, wherein the division comprises a translation of the two divided images.

2. A medical image display apparatus, as defined in claim 1, wherein the display control unit has a function for adjusting a distance between the two divided images based on an input at an input unit.

3. A medical image display apparatus, as defined in claim 1, wherein the first image is a morphological image representing morphology information about the subject, and wherein the second image is a functional image representing function information about the subject.

4. A medical image display apparatus, as defined in claim 3, wherein the morphological image is a CPR image of a tubular object, as the subject, and wherein the base line setting unit sets, as the base line, a core line of the tubular object.

5. A medical image display apparatus, as defined in claim 4, wherein the functional image represents, along the core line, the function of a surface that is orthogonal to the core line, and which is independent from a surface of the CPR image, and wherein the display control unit has a rotation display unit configured to rotate the CPR image with respect to the core line, as a rotation axis, and displays the rotated CPR image, and wherein a display of the functional image is not changed even when the rotation display unit has rotated the CPR image and displayed the rotated CPR image.

6. A medical image display apparatus, as defined in claim 2, wherein the first image is a morphological image representing morphology information about the subject, and wherein the second image is a functional image representing function information about the subject.

7. A medical image display apparatus, as defined in claim 6, wherein the morphological image is a CPR image of a tubular object, as the subject, and wherein the base line setting unit sets, as the base line, a core line of the tubular object.

8. A medical image display apparatus, as defined in claim 7, wherein the functional image represents, along the core line, the function of a surface that is orthogonal to the core line, and which is independent from a surface of the CPR image, and wherein the display control unit has a rotation display unit configured to rotate the CPR image with respect to the core line, as a rotation axis, and displays the rotated CPR image, and wherein a display of the functional image is not changed even when the rotation display unit has rotated the CPR image and displayed the rotated CPR image.

9. A medical image display method comprising the steps of:

generating a first image and a second image of a subject generated based on volume data;

setting a base line in the generated first image;

dividing, based on a division line, which is set within the second image, corresponding to the base line that has been set in the first image, the second image into two divided images; and displaying the two divided images, which have been divided, on the first image at a display device in such a manner that the two divided images are away from the base line within the first image by a predetermined distance, wherein the division comprises a translation of the two divided images.

10. A non-transitory computer-readable recording medium stored therein a medical image display program for causing a computer to execute the procedures of:

generating a first image and a second image of a subject generated based on volume data;

setting a base line in the generated first image;

dividing, based on a division line, which is set within the second image, corresponding to the base line that has been set in the first image, the second image into two divided images; and displaying the two divided images, which have been divided, on the first image at a display device in such a manner that the two divided images are away from the base line within the first image by a predetermined distance, wherein the division comprises a translation of the two divided images.

* * * * *